United States Patent [19]
Twiss et al.

[11] Patent Number: 5,375,596
[45] Date of Patent: Dec. 27, 1994

[54] METHOD AND APPARATUS FOR DETERMINING THE POSITION OF CATHETERS, TUBES, PLACEMENT GUIDEWIRES AND IMPLANTABLE PORTS WITHIN BIOLOGICAL TISSUE

[75] Inventors: Robert G. Twiss, Palo Alto; Marcia A. Ryder, San Mateo, both of Calif.

[73] Assignee: HDC Corporation, San Jose, Calif.

[21] Appl. No.: 953,072

[22] Filed: Sep. 29, 1972

[51] Int. Cl.$^5$ .................................... A61B 5/05
[52] U.S. Cl. .................. 128/653.1; 607/156; 128/903
[58] Field of Search ............ 128/898, 899, 903, 653.1; 604/53, 264, 280, 93, 95, 100; 340/853.8; 607/154, 156

[56] References Cited

U.S. PATENT DOCUMENTS

| | | | |
|---|---|---|---|
| 4,176,662 | 12/1979 | Frazer | 604/95 X |
| 4,244,362 | 1/1981 | Anderson | 128/772 X |
| 4,431,005 | 2/1984 | McCormick | 128/653.1 X |
| 4,880,414 | 11/1989 | Whipple | 604/283 |
| 4,905,698 | 3/1990 | Strohl, Jr. et al. | 128/653 |
| 4,917,094 | 4/1990 | Lynch et al. | 128 X/772 |
| 5,005,592 | 4/1991 | Cartmell | 128/653.1 |
| 5,042,486 | 8/1991 | Pfeiler et al. | 128/653.1 |
| 5,078,714 | 1/1992 | Katims | 604/264 |
| 5,099,845 | 3/1992 | Besz et al. | 128/653.1 |
| 5,146,916 | 9/1992 | Catalani | 604/280 X |
| 5,171,228 | 12/1992 | McDonald | 604/93 X |
| 5,211,165 | 5/1993 | Dumoulin et al. | 128/899 X |

Primary Examiner—Lee S. Cohen
Assistant Examiner—Samuel Gilbert
Attorney, Agent, or Firm—Lyon & Lyon

[57] ABSTRACT

A method and apparatus for determining accurately, both during and after insertion, the full length position of catheters (including implanted ports (64)), tubes (30) and placement guidewires (22) within biological tissue is disclosed including a transmitter/detector unit (2) having an alternating current (AC) radio-frequency (RF) transmitter with antenna (14), and a radio signal transmitter in the form of a continuous or segmented fine wire receiving antenna (28, 32, 74) situated along the full length of the catheter, guidewire, and implanted port assemblies (22, 30, 64). The guidewire apparatus also includes a tip antenna. These antennae are connected by a removable clip (18) to a wide-band RF detector circuit, situated within the transmitter/detector unit (2). The RF transmitter/detector circuit provides a voltage output that is a direct function of the relative spatial proximity of the transmitting antenna. This proximity is displayed visually to the operator using a sequential linear LED array (8) whose sensitivity is controlled by a gain control knob (10). An audible tone is also produced by a miniature speaker (12), and whose tone frequency is varied as a direct function of the transmitter proximity. Also shown is a method and apparatus for locating the full length position of implanted port (64) mounted catheters (72), and a method and apparatus for simultaneous infusion into an implanted port assembly 64 and detecting the full length position of the port mounted catheter (72).

17 Claims, 8 Drawing Sheets

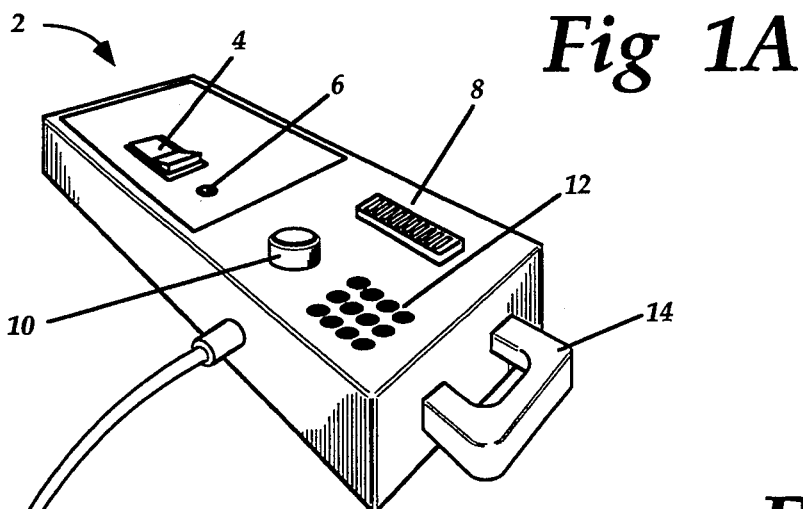
*Fig 1A*
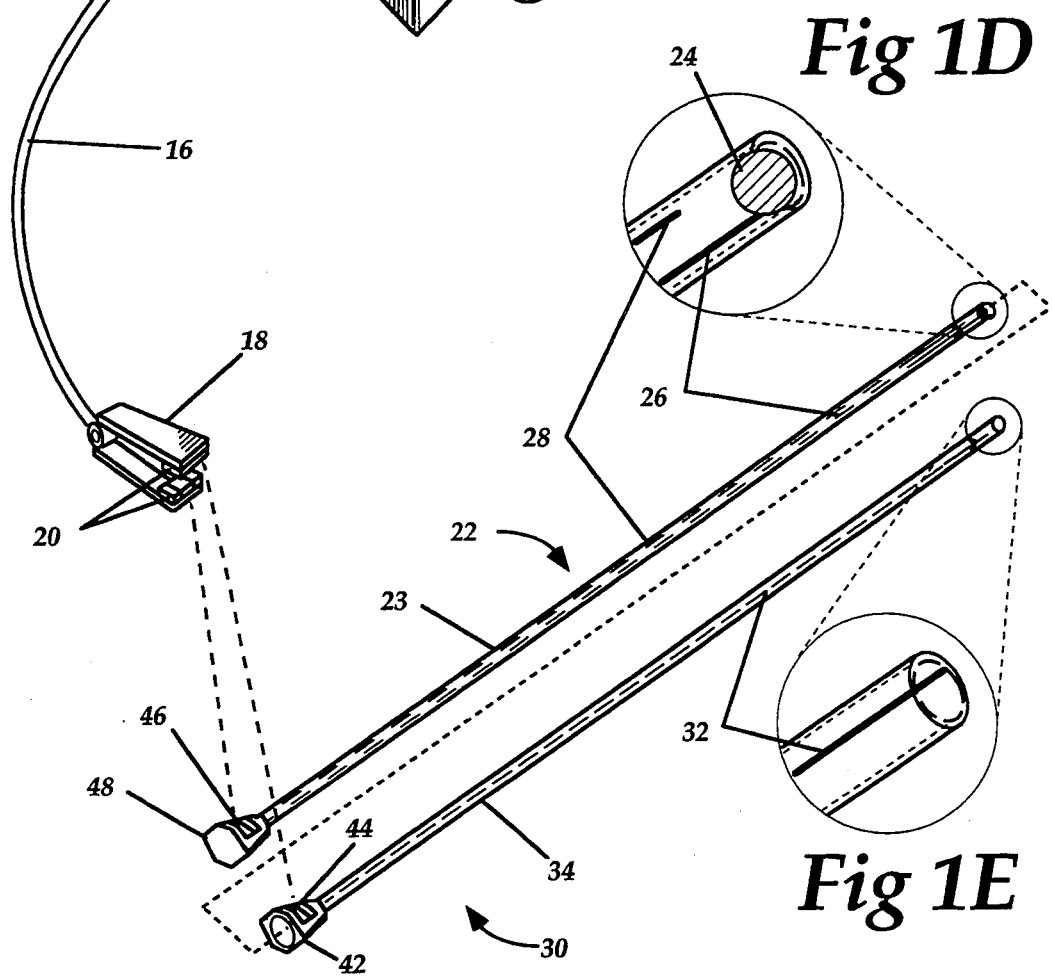
*Fig 1D*
*Fig 1E*

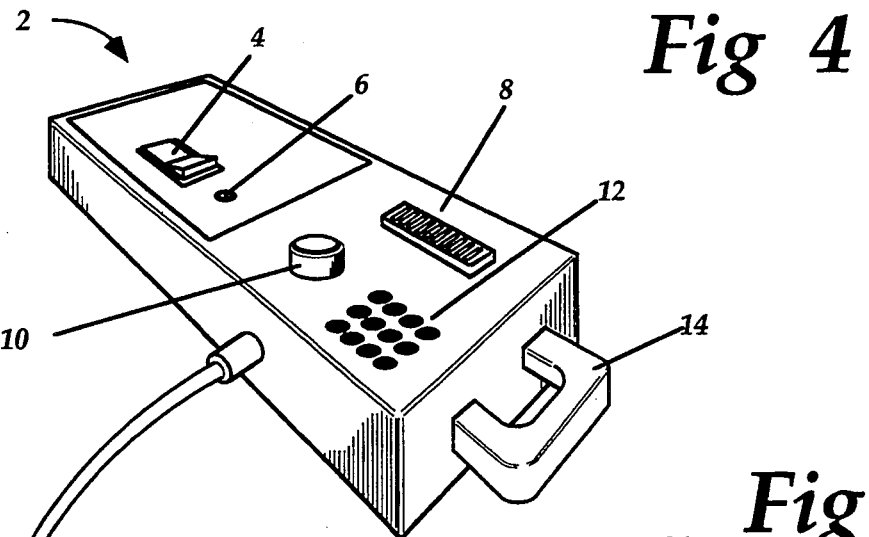
*Fig 4*
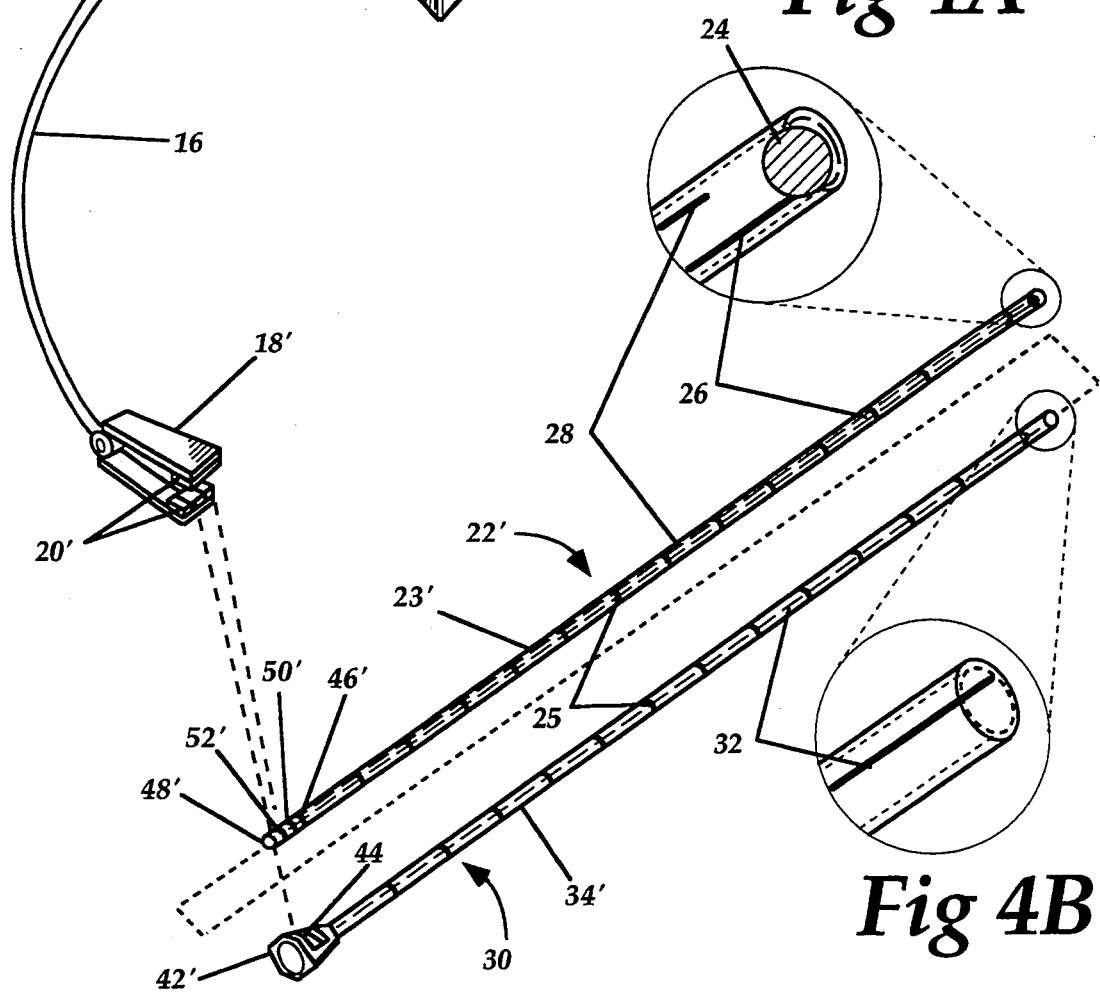
*Fig 4A*
*Fig 4B*

METHOD AND APPARATUS FOR DETERMINING THE POSITION OF CATHETERS, TUBES, PLACEMENT GUIDEWIRES AND IMPLANTABLE PORTS WITHIN BIOLOGICAL TISSUE

FIELD OF THE INVENTION

The present invention relates generally to a method and apparatus for determining accurately the full-length position of catheters, tubes, and placement guidewires inside biological tissue, particularly within veins and arteries. This method is applicable to all catheter types including implanted ports, but is especially useful for central venous catheter placement applications. This method is equally applicable for locating tubes inserted into the body, such as enteral feeding tubes.

BACKGROUND OF THE INVENTION

The placement of tubes and catheters in biological tissue is generally accomplished by a blind technique utilizing anatomical landmarks for guidance. Despite strict adherence to protocol the catheter, or tube, may deviate from the desired pathway for many different reasons, some of which are within the control of the technician and some that are not.

Methods and techniques for access to the central venous system have been well established. Hemodynamic monitoring and infusion of hyperosmolar solutions and irritating drugs requires the positioning of the catheter tip most commonly in the superior vena cava and less commonly in the inferior vena cava. Aberrant positioning of the catheter and catheter tip, either on insertion or by spontaneous migration thereafter, may result in morbid complications including venous or arterial thrombosis, pericardial tamponade, retrograde cerebral perfusion with neurotoxic symtomatology, venous perforation with thoracic or mediastinal cavity perfusion, and arrhythmias.

Gastric or intestinal positioning of various tubes are also frequently placed by a blind approach. Malposition of these tubes may result in severe consequence as well.

Current practice dictates visualization of catheters or tubes during or following insertion by radiograph or fluoroscopy. Most commonly the radiograph is taken following catheter placement to confirm proper positioning of the device, the tip in particular. Spontaneous migration can presently only be determined by repeated radiograph or fluoroscopy. Repeated exposure of the patient and medical personnel to irradiation is undesirable and costly. In addition, it is often inconvenient to move a patient to an x-ray facility or bring a portable x-ray unit to the patient either in the hospital or home, and may result in prolonging initiation of therapy.

Catheter tip-finding devices now in service can only locate the catheter tip at the time of insertion of the catheter by using a specially instrumented guidewire, however, no system is available which can trace a catheter's location after insertion. An example of such a device is disclosed in U.S. Pat. No. 4,905,698 issue Mar. 6, 1990, and assigned to Pharmacia Deltec Inc. of St. Paul, Minn. In the Pharmacia device the catheter is inserted with a guide wire mounted internal to the catheter. A part of the guidewire is a magnetic coil pick-up device at the distal end of the guidewire located within the distal end of the catheter. Once the guidewire/catheter combination is in place and the technician is assured that it is in the correct location, the guidewire is removed. To use the catheter of the Pharmacia design the guidewire must first be removed. By so doing the ability to locate the end of the catheter by the magnetic method of Pharmacia is no longer possible since the magnetic pick-up device for locating the end of the catheter is attached to the distal end of the guidewire.

It would be advantageous to not only be able to locate the tip of a placement guidewire upon insertion of the guidewire/catheter combination, but to also be able to determine the full length position upon insertion, and equally important is the ability to continually be able to monitor the location of the catheter at any time thereafter in a diagnostic manner. The later function is particularly desirable since there is no assurance that the catheter will not migrate to another location while it is still in use because of physical movements of the patient. In addition, no device is presently available which can locate the position of implanted port mounted catheters. It is important to note that tubes (such as enteral feeding tubes) inserted into the body are physically very similar to catheters and it would be advantageous to have a diagnostic location capability for them upon insertion as well as after the fact since they too can become malpositioned. The present invention clearly has all of these capabilities.

SUMMARY OF THE INVENTION

In accordance with the disclosed embodiments of the present invention there is shown a method and apparatus for continuous monitoring of the full-length path and distal end position of catheters (including implanted port models), tubes, and placement guidewires within a patient's body during initial insertion and at any time thereafter.

BRIEF DESCRIPTION OF DRAWINGS

The illustrative embodiment of the present invention may best be described by reference to the accompanying drawings where:

FIG. 1A shows a diagrammatic view of a first embodiment of a method and apparatus of the present invention for determining the full length position of catheters, tubes, and placement guidewires within biological tissue before and after removal of the guidewire.

FIG. 1D shows a magnified view of the tip of one guidewire of the present invention.

FIG. 1E shows a magnified view of the tip of one catheter of the present invention.

FIG. 4 shows a diagrammatic view of a second embodiment of a method and apparatus of the present invention for determining the full length position of catheters, tubes, and placement guidewires within biological tissue before and after removal of the guidewire.

FIG. 4A shows a magnified view of the tip of a second guidewire of the present invention.

FIG. 4B shows a magnified view of the tip of a second catheter of the present invention.

Figure 1B:
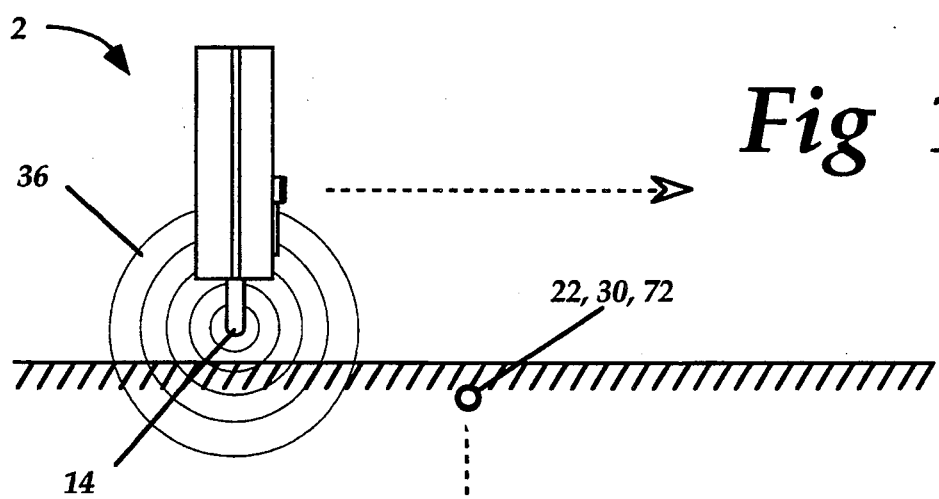
FIG. 1B schematically illustrates the use of a transmitter/detector unit together with an implanted catheter, tube or guidewire all designed according to the present invention.

All figures are drawn for ease of explanation of the basic teachings of the present invention only; the extensions of the figures with respect to number, position, relationship, and dimension of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

The same numerals designate the same or similar parts where used in the various figures.

DESCRIPTION OF THE PREFERRED EMBODIMENTS

Referring first to FIG. 1A there is shown the component parts of the first embodiment of the present invention which make it possible to determine the position of a catheter during insertion, immediately after insertion, and at any future time when the guidewire has been removed and the catheter is in use. There are three basic components to the first embodiment of the present invention: transmitter/detector unit 2 which is common to each embodiment of the present invention, guidewire assembly 22, and catheter assembly 30. This system allows a technician to determine the position, both along the entire length and the tip, of percutaneous catheters, tubes, and placement guidewires or catheters that are part of an implantable access system within veins, arteries, or other internal areas of a patient.

It is important to note that tubes (such as enteral feeding tubes) inserted into the body are physically very similar to catheters and need to be carefully positioned and that position monitorable since they too can become malpositioned. For purposes of this application any discussion of catheters also applies to tubes as a subset of catheters.

Generally, as will be described more fully below, transmitter/detector unit 2 includes a main housing having attached to the top side thereof an antenna 14 for transmitting an RF signal to be radiated to an antenna, or antennas, that are part of guidewire assembly 22 or catheter assembly 30. Transmitter/detector unit 2 also contains an internal RF alternating current (AC) generator with it's RF signal being applied to antenna 14. Internal to the housing of transmitter/detector unit 2 there is also a signal strength monitoring circuit and an annunciating device that is coupled to the antennas of either the guidewire assembly 22 or the catheter assembly 30 via cable 16 and clip 18 for monitoring the signal strength and announcing it to the technician as antenna 14 is passed over the skin of the patient in an effort to locate guidewire assembly 22 or catheter assembly 30.

As is typically done in the placement of a catheter or a tube within a vein, artery or other internal area of a patient, a guidewire, that has a smaller outer diameter than the internal diameter of the catheter or tube to be placed within the patient, is initially inserted into the catheter or tube. This is done to provide added rigidity to the catheter during the insertion procedure since catheters are generally made of a very pliable material to permit them to follow the natural internal paths through veins, arteries and other paths. In the first embodiment of the present invention, that procedure is also followed. In the second embodiment the guidewire is inserted in the patient first and when it's location has been determined to be correct the catheter is inserted by slipping it over the guidewire and when it is in the proper position the guidewire is withdrawn. It is also a common practice to insert some catheters without the aid of a guidewire. In that situation all of the monitoring functions that are split between the guidewire and the catheter in the above discussion are performed using the catheter alone to the extent possible. In any event, the actual location of the catheter will be monitorable upon insertion and at any time thereafter to confirm position of the catheter.

The construction details of the first embodiment of guidewire assembly 22 and catheter assembly 30 of the present invention can be seen by referring to FIGS. 1A, 1D and 2A, and FIGS. 1A, 1E and 2B, respectively. As shown in the figures, guidewire assembly 22 includes a pliable shaft 23 of polyurethane or a similar material (however, it would be possible to use a coiled stainless steel guidewire with the antennas being electrically insulated from the coil), and a terminal section 48. Shaft 23 has a cross-sectional size and shape along it's smallest dimension that can easily be accommodated by the interior bore of the catheter tube 34, as well as having molded therewithin two internal fine wire antennas. A first antenna 28 is an unshielded wire that extends along substantially the full length of shaft 23. Since antenna 28 is unshielded it can pick-up radiation along it's entire length when an RF signal is received thus making it possible to detect the position of guidewire assembly 22 along it's entire length. When antenna 28 is receiving radiation it can be used in combination with transmitter/detector unit 2 as discussed below for determining the path and position of guidewire shaft 23 and the surrounding catheter tube 34. The second antenna within shaft 23 includes a shielded wire 26 that extends from terminal section 48 to substantially the distal end of shaft 23. At the distal end of shaft 23, shielded wire 26 is connected to a conductive mass 24. Since wire 26 is shielded it only receives minimal radiation when exposed to it. However, since conductive mass 24 is not shielded or connected to the shield of wire 26, it can conduct radiation that it is exposed to. Since the combination of wire 26 and conductive mass 24 only receives radiation at the distal end of shaft 23, it allows for the accurate determination of the placement of the end of shaft 23, and therefore the end of tube 34 that surrounds it. When conductive mass 24 is receiving a radiated signal it can be used in combination with transmitter/detector unit 2, as discussed below, for confirming the placement of the tip of guidewire shaft 23.

Catheter/tube assembly 30 includes a pliable, thin walled elongated tubular section 34 typically of polyurethane, silastic, or a similar material, and a terminal section 42. Molded within the elongated tube section 34 is an unshielded fine wire antenna 32 that extends longitudinally along substantially the entire length thereof. Since antenna 32 is unshielded it will receive radiation along it's entire length when an RF signal is in it's vicinity. When antenna 32 is receiving a radiated signal it can be used in combination with transmitter/detector unit 2 as discussed below for determining the entire path and position of catheter tube 34. It is intended that antenna 32 will be used in post catheter/tube insertion after guidewire 22 has been removed from the interior of tube 34, however, it could also be used with guidewire 22 still in place thus making antenna 28 unnecessary. Since the use of guidewire antenna 24 and catheter antenna 32 would require the movement of clip 18, as will be seen when terminal sections 42 and 48 are discussed more completely below, it is more convenient to use the two antennas associated with guidewire 22 for the initial placement of catheter assembly 30.

It is important to note that catheters may also be constructed with both a full length antenna and a shielded wire and conductive tip pair as for the guidewire described above without departing from the scope of the present invention.

Figure 2A:
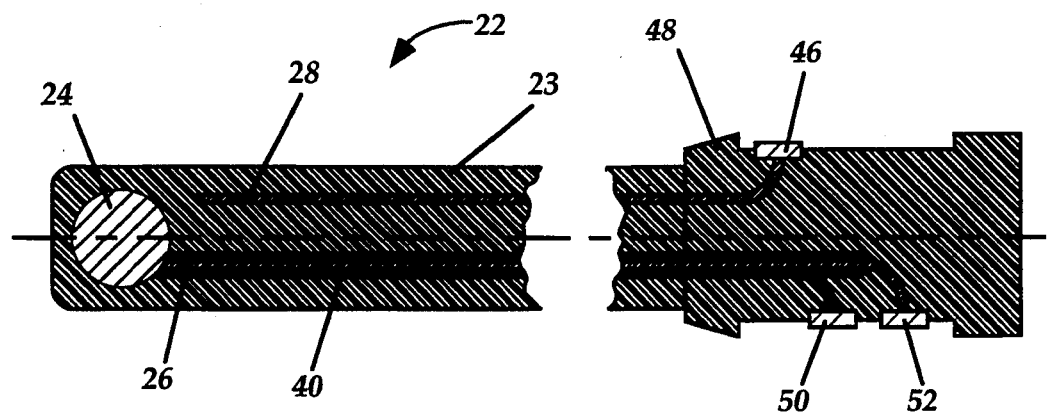
FIG. 2A is a longitudinal cross-sectional view of a first embodiment guidewire assembly of the present invention.

Referring now specifically to FIG. 2A, antenna 28 and the wire within shield 40 each typically have a diameter in the range of 0.006 inches (0.152 mm), and conductive mass 24 at the distal end of shaft 23 is typically a disk of a conductive material with a diameter in the range of 0.020 (0.508 mm). While a fine wire is the preferred antenna implementation, a thin strip of conductive film or foil could alternatively be used with equal effect. Connected to the proximate end of shaft 23 is terminal section 48 to provide a platform to which to connect clip 18 of transmitter/detector unit 2 to couple RF signals received by antennas 28 and 24 thereto. To interface with the jaws 20 of clip 18, terminal section 48 has formed therein two opposing notches sized and shaped to receive the two opposing jaws 20 of clip 18.

In this illustrated view there is a first conductive pad 46 mounted in the notch on the top of terminal section 48 with first conductive pad 46 electrically interconnected to the proximate end of antenna 28 within shaft 23. Similarly, in the notch on the bottom of terminal section 48 there are second and third conductive pads 50 and 52 connected to shield 40 and wire 26, respectively, at the proximate end of shaft 23. A thin-film plastic insulator electrically isolates wire 26 from the conductive foil of shield 40.

Figure 2B:
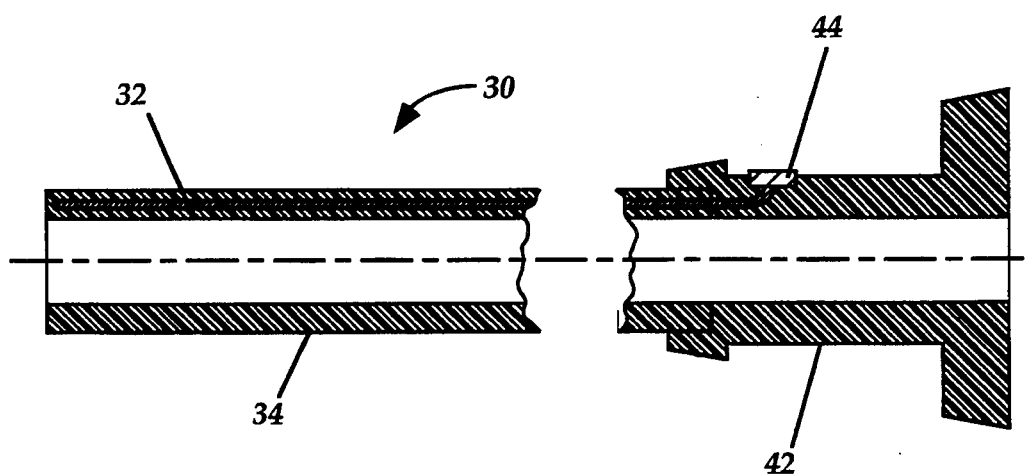
FIG. 2B is a longitudinal cross-sectional view of a first embodiment catheter or tube assembly of the present invention.

Similarly, referring now specifically to FIG. 2B antenna 32 typically has a diameter in the range of 0.002 inches (0.051 mm), and it can be seen that the proximate end of catheter tube 34 is connected to terminal section 42 to provide a platform to which to connect clip 18 of transmitter/detector unit 2 to couple RF signals to antenna 32. Since in the preferred embodiment there is only one antenna in catheter assembly 30 only one conductive pad must be provided to interface with clip 18. This is illustrated by conductive pad 44 mounted in the notch on the top of terminal section 42. Pad 44 is connected to the proximate end of antenna 32 within tube 34. Since terminal section 42, as does terminal section 48 of guidewire assembly 22, interfaces with jaws 20 of clip 18 even though catheter assembly 30 only has one conductive pad 44, terminal section 42 must also have two opposing notches sized and shaped to receive the two opposing jaws 20 of clip 18. Additionally, terminal section 42 must have a centrally located hole therethrough to permit the insertion of shaft section 23 of guidewire assembly 22 into the central bore of catheter tube section 34 prior to insertion of catheter assembly 34 into the patient.

Since shaft section 23 of guidewire assembly 22 is to be inserted into the internal bore of tube section 34 of catheter assembly 30 through terminal section 42, the length of shaft section 23 must be at least as long as, and usually longer than, the combined length of tube section 34 and terminal section 42 so that the distal end of shaft section 23 at least aligns with, and typically protrudes from, the distal end of tube section 34 at the time of insertion of catheter assembly 30 into the patient.

Alternatively, the RF signal could be applied to antennas 24, 28 and 32 instead of being radiated from antenna 14 and the same results would be achieved. However, for safety reasons it is probably more advantageous to apply the RF signal to antenna 14 and to detect the radiation with the implanted antennas as discussed above.

Antenna 14 (see FIG. 1A) is designed to transmit an AC magnetic field with the preferred form of antenna 14 being a coil in a "U"-shaped enclosure that extends outward from the body of transmitter/detector 2. Typically antenna 14 will radiate a signal in the range of one-half to one watt at a preferred frequency in the 100 kilohertz to 150 megahertz range with sections of antenna 14 being shielded and grounded to tailor and/or confine the transmitted RF field.

In use, as shown in FIG. 1B, antenna 14 is positionable near the surface of the patient's skin with the magnetic flux lines 36 projecting radially into the patient's body. As antenna 14 is passed over the patient's skin surface the RF field 36 is detected by either of the guidewire antennas 24 and 28 or catheter/tube antenna 32, depending on whether clip 18 is connected to terminal section 48 or 44.

Clip 18 and cable 16 are provided to couple any RF signals received by the antenna(s) to which it is connected to transmitter/detector 2. Any received RF signals are then processed to provide visual and audible signals as to the relative spatial proximity of the transmitter antenna 14 and antennas 24, 28 or 32.

Transmitter/detector 2 in the most usable configuration will take the form of a self-contained hand-held unit that contains RF transmitter and detector circuits, operator user interfaces, and a rechargeable power supply system and batteries. As stated above, antenna 14 in such a unit is mounted externally in a "U"-shaped fashion. This shape of antenna 14 thus emits a cylindrical field 36, and also effectively lessens hazards posed by a single, rod type antenna. Alternatively, antenna 14 could be a hand-held unit that is connected to a fixed-base transmitter/detector unit by an interconnecting cable.

Figure 1C:
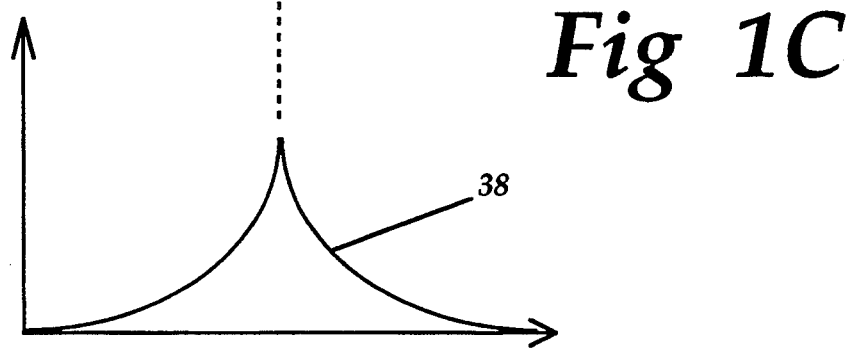
FIG. 1C illustrates the signal response of the apparatus of the present invention produced in the detector unit as it is swept over the patient in which a catheter, tube or guidewire of the present invention has been placed.

In use, as illustrated in FIGS. 1B and 1C, antenna 14 of transmitter/detector 2 is passed over the surface of the patient's skin and RF field 36 radiates into the tissue of the patient. As that radiation is received by the antennas in either guidewire shaft 23 or catheter tube 34 a signal is conducted to the detector circuit within transmitter/detector 2 by clip 18 and cable 16. The detector circuit then in response to the received signal generates a visual and an audible indication which varies as does the characteristic signal response curve 38 as illustrated in FIG. 1C, with a peak audible or visual response that coincides with the sharp signal peak generated when antenna 14 is directly above guidewire assembly 22 or catheter/tube assembly 30. When the peak is reached and then begins to drop again, transmitter/detector 2 can be moved back and forth to find the point at which the peak signal is discovered. By discovering the peak signal location the user knows that the guidewire or catheter is directly beneath that point on the surface of the patient's skin.

Since antennas 24, 28 or 32 are generally in the "near field" region of the signal transmitted from antenna 14, the received signal strength varies approximately as the cube of the distances between the transmitting and receiving antennas. An additional crucial benefit is that the orientation of the catheter, tube, or guidewire segment at any point may be inferred by rotating antenna 14 longitudinally above the patient's skin. The detected signal strength will be at a maximum when antenna 14 is aligned with the antenna mounted in the catheter, tube, or guidewire. In this way, transmitter/detector 2 provides not only the full length path determination, but individual segment orientation information of the guidewire or catheter as well.

By performing this technique while monitoring the signal from guidewire antenna 28 or catheter antenna 32, the actual location of the entire path of the guidewire or catheter can be determined. Similarly, if this technique is performed while monitoring the signal received by guidewire antenna 24 the position on the surface of the skin beneath which the end of the guidewire is located can be determined.

Figure 3:
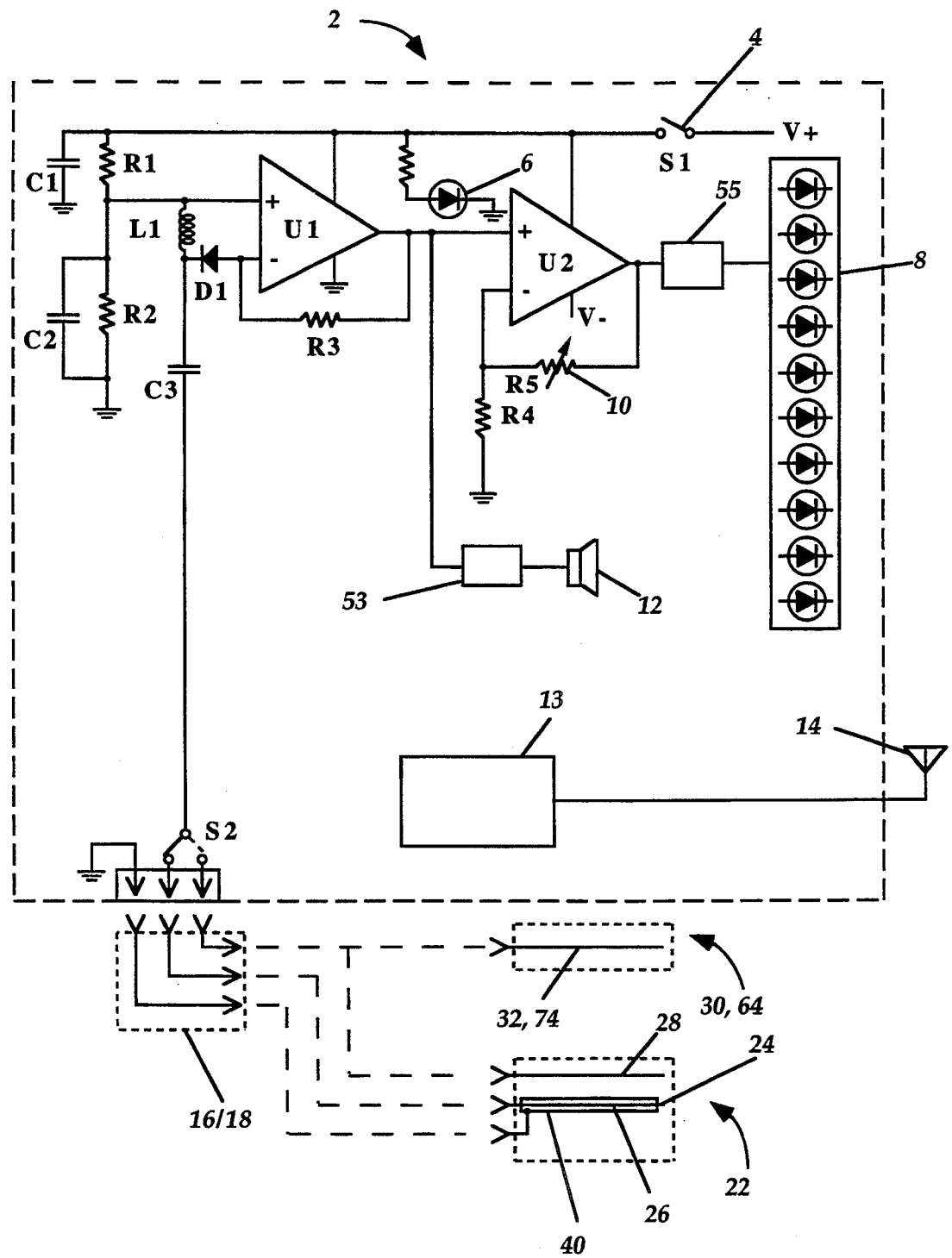
FIG. 3 is an electrical schematic representation of the detector unit of FIG. 1.

FIG. 3 is a schematic illustration of a circuit that can be used for the transmitter and detector functions of transmitter/detector 2 with that circuit enclosed within a dotted-outline. Included is a battery power source which is indicated as +V which may also include a recharger for the battery. The power from the battery is applied to the circuitry by closure of switch 4 which causes the illumination of LED 6 to indicate that the power has been turned on. Below the dotted-outline for transmitter/detector 2, shown schematically, are cable/clip combination 16 and 18, catheter assembly 30 with included antenna 32, and guidewire assembly 22 with included antenna 28 and shielded cable 26 with attached tip antenna 24, and the possible connection between the various antennas and clip 18 shown in dotted lines. Internal to transmitter/detector 2 is a switch 82 for selecting between the two antennas within guidewire assembly 22 for the detection of the received signal.

In general, the circuit of transmitter/detector 2 can be considered to have two sections: the first section including an RF transmitter; and the second section including detection circuitry and an amplifier for driving the indicators for operator use in determining the location of the guidewire or catheter.

The first section is RF Transmitter device 13 that can be any convenient low power transmitter that meets with FCC approval. For example, that transmitter could transmit on a frequency of 46 MHz at an input power of no more than 2 watts. Such a transmitter is used in a SONY Model No. NTM-1 transmitter, or similar circuit, which was found to be satisfactory.

The second section receives the RF energy detected by one of antennas 32, 28, and 24 via cable/clip 16/18 and single-pole double throw (SPDT) analog switch S2. For the guidewire arrangement, S2 switches between the full-length and tip antennas for locating the transmitter antenna path and tip, respectively. For catheter/tube antenna 32, S2 remains in the position shown, and for guidewire antennas 24 and 28, S2 must be set to the position that corresponds to the antenna which the user wishes to monitor depending on what information the user is interested in. While not shown here, it may be appreciated that S2 can be automated with a digital switch to automatically switch between full-length and tip-finding modes of the guidewire assembly to provide real-time path and tip location determination. From S2, the received RF signal passes through blocking capacitor C3 which serves as a high-pass filter to block DC signal amplification. The RF signal is detected by inductor L1 and sampled by diode D1, which rectifies the AC of the RF signal to DC and feeds it to the negative input of op-amp U1 (e.g. Motorola type 1458). Op-amp U1 then produces an output voltage that is proportional to the signal strength of the received RF signal. This voltage is then applied to the positive input of op-amp U2 (e.g. Fairchild type 741 wired in a non-inverting mode) and a voltage to frequency converter chip 53 (e.g. Analog Devices type AD537). Converter chip 53 produces an audible frequency signal the frequency of which is proportional to the input voltage. The audible frequency signal from chip 53 is then applied to speaker 12 to enable the technician to hear the tone. For simplicity, the tone volume and frequency controls for varying same have been omitted from this circuit, however they are well known in the art. Op-amp U2 has been included to process the signal from op-amp U1 to provide the visual display information of the received signal. The gain of op-amp U2 is set by resistors R4 and R5, with resistor R5 being variable and used as gain control 10. In the preferred embodiment of his circuit, the maximum gain setting is in the range of 25 which produces approximately a +5 Volts full-scale on the output terminal of op-amp U2. This voltage is then applied to LED driver chip 55 (e.g. National Semiconductor type 3914 Dot/Bar Display Driver). Chip 55 compares the output voltage from op-amp U2 to an internal reference voltage and proportionally illuminates a display of a plurality of devices, or one that is capable of indicating signal relative strength, for example by means of a plurality of LEDs or LCDs or a bar graph, with the intensity of the display being directly proportional to the strength of the received signal.

Two signaling methods are provided for the operator: a linear LED array 8 and an audible tone from speaker 12. The linear LED array 8 is moderated by variable gain control resister R5 to which knob 10 is affixed and displays the detected signal strength, and hence the relative proximity of transmitting antenna 14 to the receiving antennas 24, 28 and 32. As antenna 14 is brought closer to the receiving antennas being monitored, a varying number of LEDs in array 8 are illuminated in sequence in a bar graph fashion, and extinguish sequentially as antenna 14 passes away from the receiving antenna being monitored. Similarly, speaker 12 emits a tone whose frequency varies as a function of the proximity of antenna 14 to the receiving antenna being monitored. As antenna 14 approaches the receiving antenna being monitored, the frequency of the tone increases, and as antenna 14 moves away from the receiving antenna being monitored the frequency of the tone decreases, both in proportion to the proximity of antenna 14 to the receiving antenna being monitored.

Once the guidewire/catheter combination is in the desired position, guidewire assembly 22 may simply be withdrawn from catheter assembly 30 by pulling on terminal section 48 of the guidewire assembly and then disposed of. To diagnostically monitor the post-insertion catheter or tube location, the operator merely connects the removable clip 18 to the exposed catheter terminal section 42 and sweeps antenna 14 over the patient as in the guidewire method. Specifically, the operator may start at catheter terminal section 42 and sweep outward along the expected catheter/tube path, or sweep specific areas of interest to ensure that the catheter or tube has not migrated from its intended position. This diagnostic method is advantageous because it is non-invasive and may be performed without unduly disturbing the catheter.

The second embodiment guidewire and catheter assemblies 22' and 34' are shown in detail in FIGS. 4, 4A, 4B, 5A and 5B. In each case they are substantially the same as their first embodiment equivalents except for the fact that catheter/tube assembly 34' can be inserted over guidewire assembly 22' after guidewire assembly 22' has been placed in the desired tissue location. The differences between the two embodiments are strictly to permit that operation, otherwise the general features of each are the same. To enable that technique, terminal portion 48 of the first embodiment guidewire has been replaced with terminal portion 48' and terminal portion 42 of the first embodiment catheter has been modified to terminal portion 42' to accept a modified clip 18' which has been modified to interface with modified guidewire terminal portion 48'.

Figure 5A:
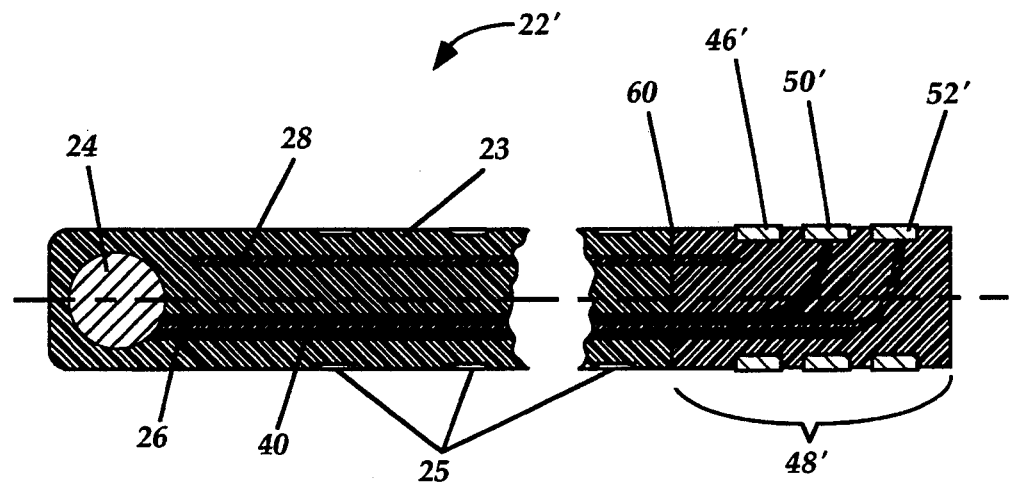
FIG. 5A is a longitudinal cross-sectional view of a second embodiment guidewire assembly of the present invention.
Figure 5B:
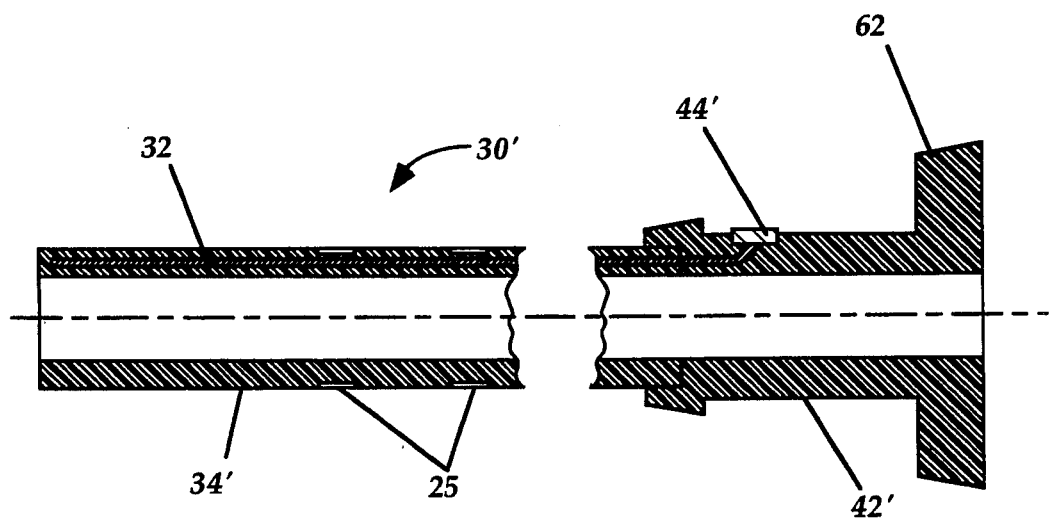
FIG. 5B is a longitudinal cross-sectional view of a second embodiment catheter or tube assembly of the present invention.

Since the modifications to the guidewire terminal portion are controlling of the other modifications, attention is first directed to FIG. 5A where the specific details of the second embodiment of guidewire assembly 22' are shown. As can be seen by comparing FIGS. 2A and 5A the only differences are in the configuration of terminal portion 48'. As can be seen in FIG. 5A terminal portion 48' is of the same diameter of shaft 23 with three concentric parallel conductive rings 46', 50' and 52' which in function correspond to contacts 46, 50 and 52 in FIG. 2A. To mate with rings 46', 50' and 52' the conductive pads (not shown) within jaws 20' of clip 18' will have to be oriented to mate with them (e.g. the contacts in jaws 20' might be oriented such that rings 46' and 52' are mated with by the top jaw and ring 50' mate with by the bottom jaw). Additionally, terminal portion 48' must extend from the proximate end of modified catheter terminal portion 42', as shown in FIG. 5B, after catheter tube 34' is slid over guidewire 22' and thereby inserted into the tissue of the patient. This is necessary so that clip 18' can be connected to terminal portion 48' when both the catheter and the guidewire are in place.

By comparing FIGS. 2B and 5B it can be seen that only terminal portion 42' has been modified to except the modified jaws 20' of clip 18' so that the same contact pad in top jaw 20' mates with conductive pad or ring 44' which is in the same location on terminal portion 42' as is ring 46' on modified guidewire terminal portion 48'.

To enable the technician to align the distal end[a] of said catheter/tube 30' with the distal end of said guidewire 22' when catheter/tube 30' is inserted into the patient by sliding it over said guidewire 22' ruled guide stripes 25 are molded into or printed onto the external surfaces at regular intervals to show the relative segment lengths of the inserted guidewire and catheter so that the detected end of guidewire 22' will correspond to the end of catheter/tube 30'. Alternatively, a line 60 could be included near the proximate end of guidewire 22' so that the length of guidewire 22' from it's distal end to line 60 is substantially the same as the combined length of catheter 34' and terminal portion 42'. In this configuration to align the distal ends of guidewire 22' and catheter tube 34' as catheter 30' is insert over guidewire 22', the proximate end 62 of terminal portion 42' of catheter/tube 30' must be substantially aligned with line 60 near the proximate end of guidewire 22'.

The rest of the features of the second embodiment are the same as those of the first embodiment and function in the same way.

Referring now to FIGS. 6A–6D and 7A–7C there is shown an implanted port and associated component parts which make it possible to determine the position of an implanted port and corresponding catheter during insertion, immediately after insertion, and at any future time the port/catheter is in use.

Figure 6A:
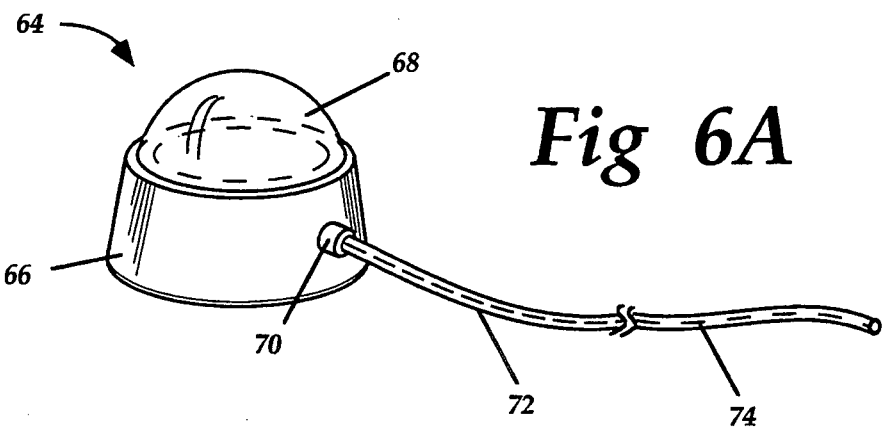
FIG. 6A is diagrammatic view of an implanted port and catheter assembly of the present invention for determining the full length position of implanted port mounted catheters.

FIG. 6A is an isometric external view of an implanted port assembly 64 of the present invention. Port assembly 64 includes a port body 66 made of polyurethane, or a similar material, on which is mounted a domed cover 68 made of silicone rubber, or a similar material. Domed cover 68 is provided to allow insertion of a needle, or similar device, to infuse liquids into port body 66 while also maintaining a seal to preclude bodily fluids from entering the port body 66 during infusion and after the infusion needle is withdrawn. Attached to port body 66 is an external coupling 70 which is made of polyurethane, or similar material, for rigidly coupling a catheter 72 thereto. Catheter 72 thus serves as a conduit to transfer infused fluids from port body 66 to selected locations within the body of the patient. Mounted integral within the wall of port catheter 72 is a fine antenna wire 74 that runs substantively the full length of port catheter 72 with antenna 74 being of a design that is similar to the previously discussed antenna embodiments.

Figure 6B:
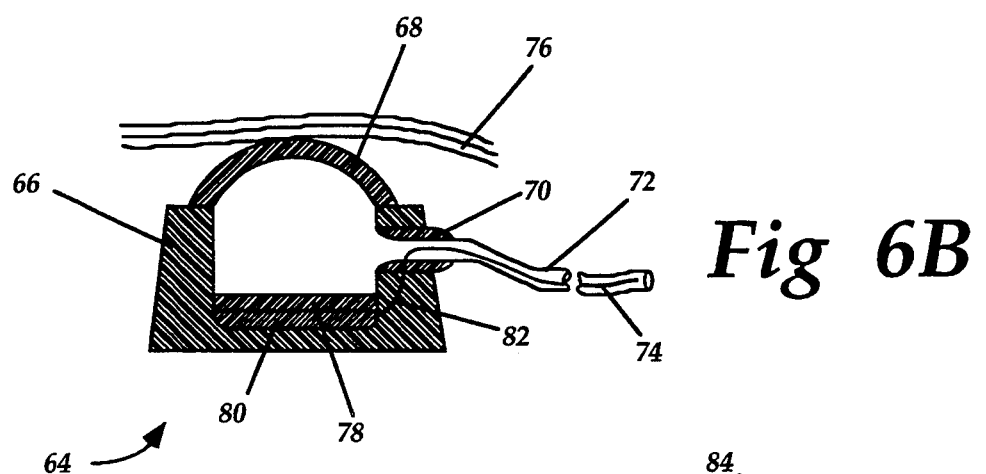
FIG. 6B is a longitudinal cross-sectional view of the in situ implanted port catheter assembly of FIG. 6A placed underneath the skin of a patient.

Referring next to FIG. 6B there is shown a cross-sectional view of an implanted port assembly 64 placed beneath a patient's skin 76. Additional features of the port assembly of the present invention can be seen in this figure, including the internal cavity of port body 66 being in the shape of a round well, however, it can be in any convenient shape. At the bottom of the well is a layer of a fine conductive mesh 80 made of copper, stainless steel, or a similar material. Above the layer of conductive mesh 80 is a sealant layer 78 of silicone rubber, or similar material, to prevent infused liquids from coming into contact with the layer of conductive mesh 80. Through the wall of port body 66 and external coupling 70, conductive mesh layer 80 is electrically connected to catheter antenna wire 74 by a transfer wire 82 of shielded copper, or a similar material.

Figures 6C, 6D:
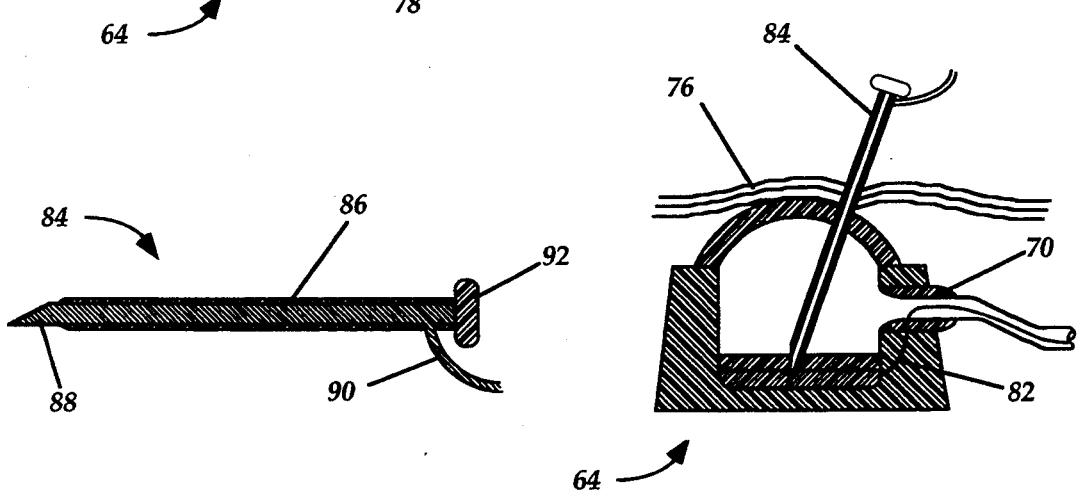
FIG. 6C is a longitudinal cross-sectional view of the port access needle assembly of the implanted port catheter of the present invention for connecting the implanted port catheter assembly of FIGS. 6A and 6B to the external detector unit described in FIGS. 1A and 4.
FIG. 6D is a longitudinal cross-sectional view of the port access needle assembly of FIG. 6C inserted through the patients' skin and into the implanted port and catheter assembly of FIG. 6B.

Next, in FIG. 6C there is shown a cross-sectional view of a port access needle 84 of the present invention. Port access needle 84 includes a cylindrical conductive core 88 having a sharp-tipped distal end with core 88 made of stainless steel, or a similar material, housed within a non-conducting insulator sheath 86 made of Teflon, or a similar material. The proximate end of insulator sheath 86 is capped by a button 92 with sheath 86 made of polyurethane, or a similar material, with button 92 being provided to aid the technician in the gripping and inserting of port access needle 84 into the well of port body 66. Electrically connected to conductive core 88 and extending outward through insulator sheath 86, just below button 92, is shielded signal cable 90. The other end of cable 90 plugs into the transmitter/detector unit 2 in a similar fashion as the conductive clip assembly 18 and cable 16 as in FIG. 1A as discussed above.

The view in FIG. 6D is similar to that of FIG. 6B with the addition of port access needle 84 inserted through the patient's skin 76 and into port assembly 64. This is done to determine the positioning of catheter 72 that is attached to implanted port assembly 64 in much the same way as discussed above for the first two embodiments of the present invention. On insertion, the tip of the port access needle 84 penetrates skin 76, pierces domed cover 68, passes through sealant layer 78, and terminates within conductive mesh layer 80. In this way, the detector circuit of transmitter/detector 2 is connected electrically connected to catheter antenna wire 74, in sequence through signal cable 90, conductive core 88, conductive mesh 80, and transfer wire 82. Hence, the detector of transmitter/detector unit 2 is free to receive RF energy from transmitter antenna 14 mounted on the transmitter/detector unit 2 in an identical manner as the previously discussed catheter and guidewire mounted antenna embodiments. The method for locating implanted port mounted catheters is identical to the method previously discussed for locating catheters, tubes, and placement guidewires.

Figure 7A:
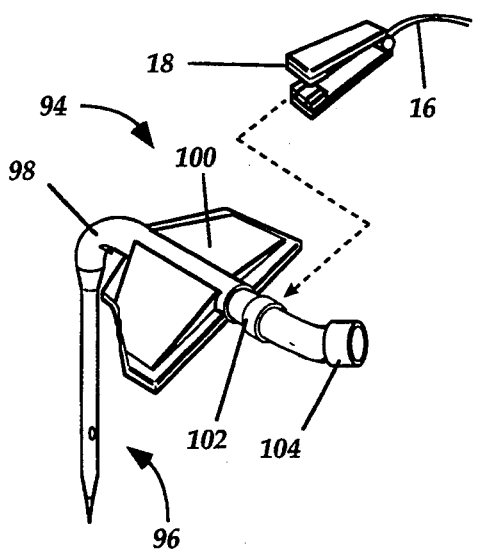
FIG. 7A is a diagrammatic view of an infusion needle assembly of the present invention for use with the implanted port of FIG. 6B to simultaneously allow infusion of fluid into the implanted port catheter assembly and determination of the full length position of the implanted port assembly catheter of the present invention.
Figure 7B:
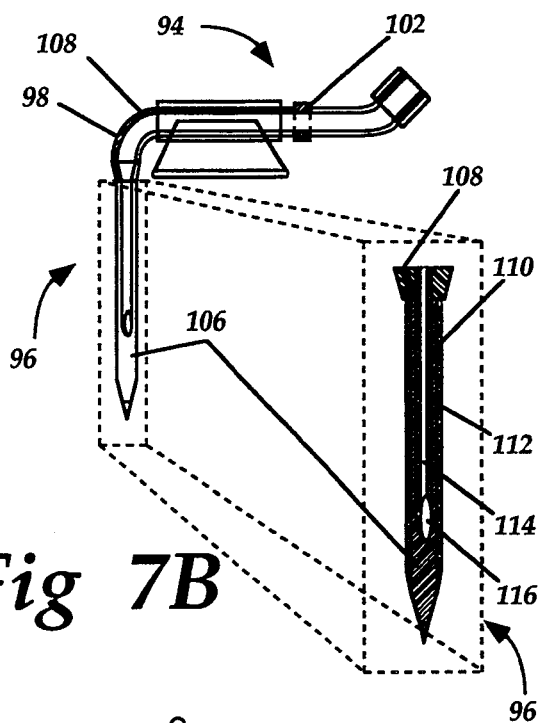
FIG. 7B is a longitudinal cross-sectional view of the infusion needle assembly of FIG. 7A, including an enlarged view illustrating key needle details.
Figure 7C:
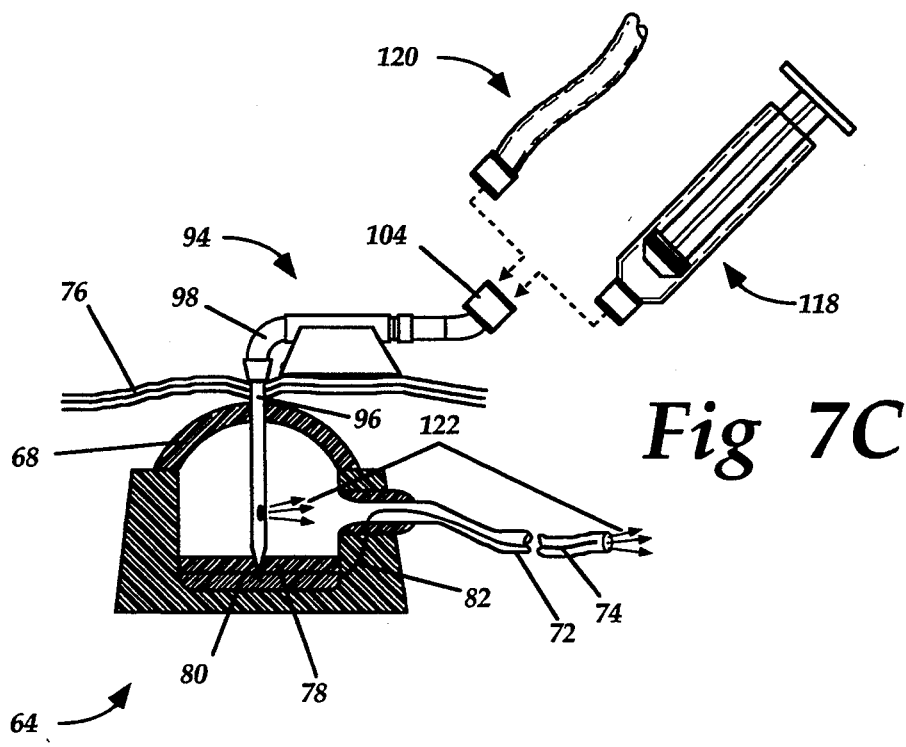
FIG. 7C is a longitudinal cross-sectional view of the infusion needle assembly and the implanted port catheter of the present invention with the needle inserted through the skin of a patient into the implanted port catheter assembly and the alternative interface between an infusion syringe and infusion drip line components.

Referring to FIGS. 7A–7C there is shown an infusion needle assembly 94 for use with implanted port assembly 64, both of the present invention. As will be seen in the following discussion, the infusion needle assembly 94 makes it possible to simultaneously infuse liquids into the implanted port catheter assembly 64/72 and to determine the full length position of the implanted port mounted catheter 72 during insertion and at any time thereafter.

Referring first to FIG. 7A there is shown an isometric view of a port infusion needle assembly 94 of the present invention. The component parts of the assembly are needle 96 connected to the distal end of "L"-shaped fluid tube 98 which is mounted on the placement pad 100 in the central portion of tube 98. Placement pad 100 is optional, however, if it is utilized it can aid in the stabilization of infusion needle 96 when it is installed. Between the central portion and the proximate end of fluid tube 98 there is a conductive ring 102, and at the proximate end of tube 98 there is a tube receptacle 104. As described more completely below, conductive ring 102 provides the interconnection site between transmitter/detector 2 and catheter antenna 74 via conductive clip 18 and cable 16 (see FIG. 1A).

FIG. 7B is provided to show a longitudinal cross-sectional view of the infusion needle assembly 94 on the left side, and an enlarged inset of a cross-sectional view of needle 96 on the right side. It can be seen that needle 96 includes an electrically conductive core 106 made from stainless steel, or similar material, that, except for the distal tip, is coated on the exterior with a non-conductive sheath 110 of Teflon, or similar material. In the center of conductive core 106 and extending longitudinally along about three-quarters of the length thereof toward the tip, there is a central cavity 114 that is disposed to be connected to the distal end of fluid tube 98. Additionally, central cavity 114 is in communication with a needle port 116 at the furthest distance from fluid tube 98 that extends outward through conductive core 106 and non-conductive sheath 110 to the side of needle 96 about one-quarter of the distance from the tip thereof. The interior of central cavity 114 and needle port 116 is coated on the interior with Teflon, or similar material, 112 and seals with non-conductive sheath 110 on the exterior of needle 96. Thus, in this configuration, the outer surface of needle 96 is only electrically conductive at its tip at the distal end, in much the same manner as port access needle 84 described previously. To interconnect needle 96 with transmitter/detector 2, conductive core 106 is electrically connected to conductive ring 102 via transfer wire 108 which is shielded copper, or similar material, that travels along the length of the exterior of fluid tube 98 and is connected to conductive core 106 interior to non-conductive sheath 110.

Then in FIG. 7C there is shown infusion needle assembly 94 with needle 96 inserted through both the patient's skin 76 and dome 68 extending into the interior well of implanted port assembly 64. To stabilize infusion needle 96, tube 98 can be taped in place on the skin of the patient, or, if placement pad 100 is used it is placed in contact with the patient's skin and a piece of adhesive tape placed over it to prevent needle 96 from moving or becoming dislodged from implanted port assembly 64.

To infuse liquids into the patients' body once needle 96 is in place, the technician may attach an infusion syringe 118 or a drip line 120 to tube receptacle 104 introducing fluid into port assembly 64 via tube 98 and needle 96. This occurs as the fluid travels through fluid tube 98 and central cavity 114 and exits needle 96 to the side through needle port 116 into the well of infusion port assembly 64. The infused fluid then travels outward from the well of port body 66, through external coupling 70 and then through catheter 72 to the desired location within the patients' body. The fluid flow 122 is shown illustratively in FIG. 7C by means of the arrows within the well of infusion port assembly 64 and from the end of catheter 72.

To determine the location of catheter 72 once infusion needle assembly 94 is in place, the technician places clip 18 onto conductive ring 102, in much the same manner as for the catheter and guidewire contacts for the first and second embodiments described previously. The technician then sweeps the body with transmitter/detector unit 2 in a similar fashion to that described previously for the other embodiments of the present invention.

In keeping with the theme of the present invention it should be obvious that the present invention includes the possibility of threading a wire down the internal cavity of an implanted catheter, some distance which maybe less than the full length of the catheter, and using that wire to either radiate or detect an RF signal to make it possible to locate the catheter position using the equipment and method of the present invention. Therefore such a threaded wire is to be included in the definition of a guidewire as discussed above. When discussing the relative motion between the radiating and detecting antennas it should be understood that motion can be created be mechanical motion between the antennas or by making one of the antennas be an antenna array with the signal switched electrically through the array to make it appear that there is physical motion between the antennas, therefore this is included in the definition of providing relative motion between the antennas. Additionally, the discussion above has generally referred to full length antennas or the detection of the end of the catheter or guidewire from a conductive mass at the distal end thereof. The same technology and equipment that has been modified slightly can be used to detect the position with an antenna that is less than the full length of the catheter or guidewire, or from conductive masses that are placed at selected locations along the catheter or guidewire, e.g. at locations that are ¼, ½, or ¾ of the full length. These too should be considered to be part of the method and apparatus of the present invention and included in the definition of catheter and guidewire of the present invention. Still further, the catheter and tube that were described above where of the type that have a central hole extending longitudinally therethrough, and there are some catheter and tube designs that have a blind end with exit ports through the side walls. The same techniques described above are also applicable to catheters and tubes of that design. Finally, there may be a need to exchange a catheter once it has been installed since they sometimes become infected. To perform that exchange a guidewire that is at least a few centimeters longer than the catheter is inserted into the catheter that is to be withdrawn and they both are withdrawn leaving several centimeters of the guidewire in place following the removal of the catheter and then the new catheter is inserted over the guidewire and the combination inserted in the same way that the original catheter was inserted. In this situation, or in any insertion situation, it might be desirable to check the location of a portion of the catheter or guidewire before it is fully inserted. That operation is also part of the present invention and the claims are to be interpreted to cover that situation as well.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the broadest interpretation of the appended claims, rather than being limited to the embodiments shown and discussed in the foregoing description, and all changes which come within the meaning ,and range of equivalency of the claims are intended to be embraced therein.

What is claimed is:

1. A system for assisting in the placement and location of previously inserted catheters, tubes or placement guidewires inside biological tissue, wherein each of said catheters, tubes or placement guidewires have a proximate end and a distal end and a predefined first length therebetween, said system being able to determine a location of said catheters, tubes or placement guidewires inside biological tissue in close proximity thereto at any point anywhere along the first length thereof, said system comprising in combination:

at least one of a catheter, tube or placement guidewire each being formed of a flexible solid material of a measurable thickness along the predefined first length thereof having;

a first antenna being a flexible dipole having a proximate and a distal end defining a selected second length therebetween contained individually within said flexible solid material of each of said at least one of a catheter, tube or placement guidewire with the proximate ends of said flexible solid material and said first antenna in alignment, with said first antenna extending along at least a portion of the length of each of said at least one catheter, tube or placement guidewire to receive or transmit an RF signal along the selected second length of the flexible dipole; and a first connector mounted on said proximate end of each of said at least one of a catheter, tube or placement guidewire and connected to said proximate end of said first antenna with the distal end of said first antenna being otherwise free of connection; and a detector/transmitter including:

a second antenna to receive or transmit an RF signal between itself and said first antenna external to said biological tissue in which each of said at least one of a catheter, tube or placement guidewire is located;

an RF transmitter to generate an RF signal;

a first conductor connected to apply said RF signal from said RF transmitter to one of said first and second antennas;

a detector to determine the strength of said RF signal being coupled electro-magnetically between said first and second antennas as said second antenna of said transmitter/detector is brought into proximity of said first antenna within each of said at least one of a catheter, tube or placement guidewire in place within said biological tissue;

a signaling device coupled to said detector to provide an indication to the user of a strength of said RF signal coupled between said first and second antennas; and a second connector disposed to couple with said first connector to couple said RF signal between said first antenna and said detector/transmitter.

2. The system as in claim 1 wherein said signaling device includes a visual display to provide an indication of the strength of said RF signal as a function of the proximity between said first and second antennas.

3. The system as in claim 1 wherein said signaling device includes an enunciator to generate a signal audible to the user that increases or decreases in volume or frequency as the strength of said RF signal increases or decreases, respectively, as a function of the proximity between said first and second antennas.

4. The system as in claim 1 wherein said detector/transmitter includes a housing outward from which extends said second antenna with said second antenna having a selected shape.

5. A system for assisting in the placement and location of a previously inserted placement guidewire inside biological tissue, wherein said placement guidewire has a proximate end and a distal end and a predefined first length therebetween, said system being able to determine a location of a selected point along the length of said placement guidewire inside biological tissue in close proximity thereof, said system comprising in combination:

a placement guidewire being formed of a flexible solid material and being of a measurable thickness along the predefined first length thereof, said placement guidewire having;
     a first antenna contained within said flexible solid material of said placement guidewire including:
       a conductive mass located at a selected point along the length of said placement guidewire to receive or transmit an RF signal;
       a first coaxial cable having an outer shield and a central conductor with only said central conductor being connected to said conductive mass, and said first coaxial cable extending from said selected point to said proximate end of said placement guidewire;
     a first connector mounted on said proximate end of said placement guidewire and thereat individually connected to each of said outer shield and central conductor at the proximate end of said first coaxial cable with said conductive mass being otherwise free of connection; and
   detector/transmitter including:
     a second antenna to couple an RF signal between itself and said first antenna external to said biological tissue in which said placement guidewire is located;
     an RF transmitter to generate an RF signal;
     a first conductor connected to apply said RF signal from said RF transmitter to one of said first connector and said second antenna;
     a detector connecting to the one of said first connector and said second antenna to which said first conductor is not connected to determine a strength of said RF signal being coupled electromagnetically between said first and second antennas as said second antenna of said transmitter/detector is brought into proximity of said first antenna within said placement guidewire in place within said biological tissue;
     a signaling device coupled to said detector to provide an indication to the user of the signal strength of said RF signal coupled between said first and second antennas; and
     a second connector connected to said detector to couple said detector to the one of said first connector and said second antenna to which said first conductor is not connected to conduct said RF signal by electro-magnetic radiation between said first antenna and said detector/transmitter.

6. The system as in claim 2 wherein said placement guidewire further includes a third antenna being a flexible dipole having a proximate end and a distal end defining a second length therebetween contained individually within said flexible solid material of said placement guidewire with said third antenna extending along at least a portion of the first length of said placement guidewire to receive or transmit an RF signal.

7. The system as in claim 2 wherein said detector/transmitter includes a housing outward from which extends said second antenna with said second antenna having a selected shape.

8. A method for determining the path of a catheter or a placement guidewire in a catheter-placement guidewire system having a catheter and a placement guidewire, and a detector/transmitter, wherein:

each of said catheter and placement guidewire are each formed from a flexible solid material and each has a proximate end and a distal end with a predefined first length therebetween, in addition each of said catheter and placement guidewire has a first antenna being a flexible dipole having a proximate and a distal end defining a selected second length therebetween contained individually within said flexible solid material with said first antenna extending along at least a portion of the first length of each of said catheter and placement guidewire to receive or transmit an RF signal along the selected second length of the flexible dipole with a first connector mounted on said proximate end of each of said catheter and placement guidewire that is also connected to said proximate end of said flexible dipole with the distal end of said flexible dipole being otherwise free of connection in each of said catheter and placement guidewire; and
   a detector/transmitter that includes an RF transmitter, a second connector disposed to couple with said first connector of said first antenna of one of said catheter and placement guidewire to couple said RF signal between that first antenna and said detector/transmitter, a second antenna to receive or transmit an RF signal between itself and said first antenna coupled to said second connector external to said biological tissue in which each of said catheter and placement guidewire are located, a first conductor connected to apply an RF signal from said RF transmitter to one of said first antenna coupled to said second connector and said second antenna, a detector to determine a strength of said RF signal being coupled electro-magnetically between said first antenna coupled to said second connector and said second antenna as said second antenna of said transmitter/detector is brought into proximity of said first antenna within each of said catheter and placement guidewire in place within said biological tissue, and a signaling device coupled to said detector to provide an indication to the user of the strength of said RF signal coupled between said first antenna coupled to said second connector and said second antenna, said method for determining a path of said first antenna of either of said catheter or placement guidewire, anywhere along the second length of said flexible dipole of said first antenna coupled to said second connector inside biological tissue comprising the steps of:
   (a) at least partially inserting at least one of either of said catheter and placement guidewire into said biological tissue along a path that is believed to be a desired path;
   (b) connecting said first connector of one of said catheter or placement guidewire of step (a) to said second connector of said transmitter/detector;

(c) coupling an RF signal between said second antenna of said transmitter/detector outside of said biological tissue and anywhere along the selected second length of said first antenna of the catheter or placement guidewire of step (a) having the first connector to which the second connector was connected in step (c);

(d) providing relative movement between said second antenna coupled to said second connector and said first antenna as in step (c) in the expected vicinity of the path within said biological tissue taken by said catheter or placement guidewire of step (c); and (e) monitoring the indications of said signalling device to note those points where those indications reach a peak signal strength and noting the physical position of said second antenna relative to an outer surface of said biological tissue as in step (d) is performed; and (f) repeating steps (a)–(e) until as much of the path of said first antenna coupled to said second connector as in step (b) is noted as desired to the extent to which said catheter or placement guidewire has been inserted in step (a).

9. A method as in claim 8 for locating the distal end of said catheter and placement guidewire wherein each of said catheter and placement guidewire includes a third antenna being a conductive mass located within said flexible solid material at a selected point along the length of said placement guidewire to receive or transmit an RF signal and said catheter longitudinally defines an internal bore therein, a first coaxial cable having an outer shield and a central conductor with only said central conductor being connected to said conductive mass and extending from said selected point to said proximate end of said placement guidewire, and at the proximate end of said coaxial cable with said central conductor and shield thereof individually connected to said first connector on the proximate end of said placement guidewire with said conductive mass being otherwise free of connection, said method further includes the steps of:

(g) following step (f), uncoupling said second connector from said first connector;

(h) following step (g), inserting said placement guidewire having said conductive mass therein into the internal bore of the catheter with the distal end of said catheter substantially corresponding with the distal end of said placement guidewire;

(i) following step (h), coupling said second connector of said transmitter/detector to said first connector of said placement guidewire;

(j) following step (i), repeating steps (c) and (d);

(k) monitoring the indications of said signalling device to note the point where those indications reach a peak signal strength and noting the physical position of said second antenna relative to an outer surface of said biological tissue as step (d) is performed thus locating the position of said conductive mass while said placement guidewire remains within said catheter as defined above.

10. A combination of a placement guidewire and a catheter for insertion into biological tissue, said catheter having an internal bore sized and shaped to slip over said placement guidewire before or after said placement guidewire has been inserted into said biological tissue, said placement guidewire comprising:

an elongated flexible portion having a distal end and a proximate end defining therebetween a first selected length, said flexible portion being formed of a flexible solid material with a substantially uniform selected cross-sectional shape and size along said first selected length thereof, said first selected length being at least as long as said internal bore of said catheter to be slid thereover and said cross-sectional size and shape of said flexible portion being smaller than the size and shape of the internal bore of said catheter;

an antenna being a flexible dipole having a proximate end and a distal end defining a second selected length therebetween contained within said flexible solid material of said flexible portion and extending along at least a portion of the first selected length of said flexible portion with said proximate ends of said flexible dipole and said flexible solid material being aligned with each other and said flexible dipole disposed to receive or transmit an RF signal along said second selected length of said flexible dipole; and a connector having a third selected length and a cross-sectional shape and size over which a catheter, of a fourth selected length and having a proximate and a distal end, may be placed and advanced along said flexible portion and said connector is affixed to said proximate end of said flexible portion and connected to said proximate end of said flexible dipole with the distal end of said flexible dipole being otherwise free of connection wherein a combination of said first and third selected lengths is greater than said fourth selected length of said catheter, said connector being provided to permit connection to said proximate end of said flexible dipole external to said catheter when in place and when the distal ends of said catheter and said flexible portion are substantially in alignment with said connector then being external to said proximate end of said catheter.

11. A placement guidewire as in claim 10 wherein:

said flexible portion of said placement guidewire includes:

an indicator mark on said flexible portion near the proximate end of said flexible portion that when said catheter is in place and said indicator mark is aligned with the proximate end of said catheter the distal ends of said flexible portion and said catheter are substantial aligned with each other; and said placement guidewire further includes:

a conductive mass located within said flexible solid material of said placement guidewire at a selected point along said first selected length of said flexible portion to receive or transmit an RF signal; and a coaxial cable having an outer shield and a central conductor and a proximate end and a distal end with only said central conductor at the distal end of said coaxial cable being connected to said conductive mass and said proximate end of said coaxial cable being substantially aligned with the proximate end of said flexible portion, and at the proximate end of said coaxial cable, said central conductor and outer shield thereof are individually connected to said connector on the proximate end of said flexible portion with said conductive mass being otherwise free of connection, wherein when said conductive mass is located substantially at the distal end of said placement guidewire said conductive mass can be used to locate the distal end of said flexible portion and the distal end of said catheter when said catheter is in place and said indicator mark on said flexible portion is aligned with the proximate end of said catheter.

12. A combination of a placement guidewire and a catheter for insertion into biological tissue, said catheter having an internal bore sized and shaped to accept said placement guidewire therewithin, said placement guidewire comprising:

an elongated flexible portion having a distal end and a proximate end defining therebetween a first selected length, said flexible portion being formed of a flexible solid material with a substantially uniform selected cross-sectional shape and size along said first selected length thereof, said first selected length being at least as long as said internal bore of said catheter to be slid thereinto and said cross-sectional size and shape of said flexible portion being smaller than the size and shape of the internal bore of said catheter;

a flexible antenna being a flexible dipole having a proximate end and a distal end defining a second selected length therebetween contained within said flexible solid material of said flexible portion and extending along at least a portion of the first selected length of said flexible portion with said proximate ends of said flexible dipole and said flexible solid material being aligned with each other, and said flexible dipole disposed to receive or transmit an RF signal along said second selected length of said flexible dipole; and a connector affixed to said proximate end of said flexible portion and connected to said proximate end of said flexible dipole with the distal end of said flexible dipole being otherwise free of connection, said connector having substantially the same cross-sectional shape and size as said flexible portion being provided to permit connection to said proximate end of said flexible dipole.

13. A placement guidewire as in claim 12:
said placement guidewire further including:

a conductive mass contained within said flexible solid material of said flexible portion at a selected location along the first selected length of said flexible portion to receive or transmit an RF signal; and a coaxial cable contained within said flexible solid material of said flexible portion, said coaxial cable having an outer shield and a central conductor with only said central conductor being connected to said conductive mass and said coaxial cable extending from said conductive mass to said proximate end of said flexible portion; and wherein said connector also is connected to each of said outer shield and central conductor of said coaxial cable at the proximate end of said flexible portion with said conductive mass being otherwise free of connection, said connector being provided to also permit individual connection to said outer shield and central conductor of said coaxial cable external to the biological tissue into which said placement guidewire is inserted.

14. A catheter for insertion within biological tissue for internal delivery of fluids from an external source of same, said catheter comprising:

a tube portion formed of a flexible solid material, said tube of a first selected length and diameter having a proximate end and a distal end and defining a longitudinal hole therethrough;

an antenna being a flexible dipole having a proximate end and a distal end defining a second selected length therebetween contained within said flexible solid material of said tube extending along at least a portion of the first selected length of said tube portion with said proximate ends of said flexible dipole and said tube portion in alignment, said flexible dipole to receive or transmit an RF signal along the second selected length of said antenna; and a connector affixed to said proximate end of said tube portion, said connector defining a hole therethrough aligned with said longitudinal hole defined by said tube portion and connected to said proximate end of said antenna with the distal end of said antenna being otherwise free of connection, said connector being provided to permit connection to said antenna external to the biological tissue into which said catheter is inserted, as well as connection to said external source of fluids for internal delivery.

15. An implantable port/catheter assembly for insertion within tissue for internal delivery of fluids from an external source of same, said implantable port/catheter assembly comprising:

a catheter including:

a flexible tube portion of a selected outer diameter having a proximate end and a distal end defining a first selected length therebetween, and at least one of a centrally located longitudinal hole therethrough and a cavity extending thereinto with an exit port therefrom; and a flexible dipole having a distal end and a proximate end defining a second selected length therebetween with said proximate ends of said flexible tube portion and said flexible dipole in alignment and with said flexible dipole extending along at least a portion of the length of said flexible tube portion from said proximate end thereof to receive or transmit an RF signal therealong;

an implantable port including:

a well defining a blind internal cavity therewithin to receive infused liquids, said internal cavity defining a top opening and interior side and bottom surfaces thereof, said internal cavity including therewithin:

a conductive layer lining at least a portion of the bottom surface of said cavity;

a pierceable sealant layer enclosing said conductive layer to prevent said infused liquids from reaching said conductive layer;

a port above said sealant layer and extending through the side surface of said internal cavity to communicate with said proximate end of said flexible tube portion of said catheter to provide said infused liquid to said catheter; and a wire extending from said conductive material layer into said port;

a pierceable dome to enclose the top opening of said cavity of said well to prevent body fluids from entering said internal cavity of said well; and a coupler interconnecting the proximate end of the flexible tube portion of said catheter with said port to deliver infused liquids from said well to said catheter and to connect said proximate end of said flexible dipole of said catheter to said wire of said well with the distal end of said flexible dipole being otherwise free of connection.

16. An implantable port/catheter assembly as in claim 15 further including:

a non-invasive external transmitter/detector to radiate an RF signal, and to detect and determine a strength of said RF signal as received by said flexible dipole of said catheter; and a port access needle having:
 a conductive core having a proximate and a distal end with a sharpened conductive tip at the distal end thereof;
 an insulative outer layer around said core leaving only a portion of said tip exposed; and
 a connector at the proximate end of said core disposed to be connected to said external transmitter/detector to couple the signal received by said flexible dipole thereto when the tip of said port access needle has been inserted thorough said dome and said sealant layer into said conductive material layer to make contact therewith by said tip of said port access needle to complete a connection with said flexible dipole of said catheter to make it possible to locate said port/catheter assembly when liquids are not being infused thereinto.

17. An implantable port/catheter assembly as in claim 15 further including:

a non-invasive external transmitter/detector to radiate an RF signal and to detect and determine a strength of said RF signal as received by said flexible dipole of said catheter; and an infusion needle assembly having:
 a needle body having:
  a conductive core of an elongated shape with an exterior side surface and a proximate and a distal end with a sharpened tip at the distal end thereof, and said core defines therewithin a longitudinally extending interior cavity that opens to the proximate end of said core and to the side surface of said conductive core intermediate said proximate and distal ends thereof;
  an insulative coating in said cavity and on substantially all of said external side surface of said core leaving only a portion of said tip at the distal end thereof exposed; and
 a coupler connected to said core at the proximate end thereof disposed to be connected to said external transmitter/detector to couple the signal received by said antenna thereto when the uncoated distal tip of said needle body has been inserted thorough said dome and said sealant layer into said conductive material layer to make contact therewith by said tip of said needle body to complete a connection with said antenna of said catheter to make it possible to locate said port/catheter assembly;
 said opening in the side surface of said conductive core disposed to be above said sealant layer when said needle body has been inserted thorough said dome and said sealant layer into said conductive material layer; and a fluid tube assembly having:
 a hollow tube with a distal end and a proximate end for conducting fluid to be infused from said external source at the proximate end to said needle body at the distal end;
 a first connector at said proximate end of said tube disposed to mate with said external source of said fluid to be infused;
 a second connector at said distal end of said tube disposed to deliver said fluid for infusion into said cavity within said conductive core of said needle body and disposed to make connection with said conductive core of said needle body;
 a third connector disposed to be connected to said external transmitter/detector; and
 a conductor to interconnect said third connector and said second connector to each other.

* * * * *